US011551351B2

(12) United States Patent
Takei (10) Patent No.: US 11,551,351 B2
(45) Date of Patent: Jan. 10, 2023

(54) PRIORITY JUDGEMENT DEVICE, METHOD, AND PROGRAM

(71) Applicant: FUJIFILM Corporation, Tokyo (JP)

(72) Inventor: Mizuki Takei, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 264 days.

(21) Appl. No.: 16/681,831

(22) Filed: Nov. 13, 2019

(65) Prior Publication Data

US 2020/0160517 A1  May 21, 2020

(30) Foreign Application Priority Data

Nov. 20, 2018  (JP) .............................. JP2018-217754

(51) Int. Cl.
  *G06K 9/00*  (2022.01)
  *G06T 7/00*  (2017.01)
  *G16H 30/00*  (2018.01)

(52) U.S. Cl.
  CPC .......... *G06T 7/0012* (2013.01); *G16H 30/00* (2018.01); *G06T 2207/10081* (2013.01); *G06T 2207/30101* (2013.01)

(58) Field of Classification Search
  CPC .................................................. G06T 7/0012
  See application file for complete search history.

(56) References Cited

U.S. PATENT DOCUMENTS

| 8,560,341 B2 | 10/2013 | Iwase et al. | |
| 9,852,269 B2 | 12/2017 | Sakagawa et al. | |
| 10,297,352 B2 | 5/2019 | Sakagawa et al. | |
| 10,552,672 B2 | 2/2020 | Iwase et al. | |
| 2013/0136326 A1 | 5/2013 | Iwase et al. | |
| 2017/0202530 A1* | 7/2017 | Mainprize | A61B 6/461 |
| 2017/0262600 A1* | 9/2017 | Park | G16H 50/20 |
| 2019/0122073 A1* | 4/2019 | Ozdemir | A61B 6/5217 |
| 2019/0228524 A1* | 7/2019 | Chen | G06K 9/6227 |
| 2020/0279649 A1* | 9/2020 | Kadir | G06K 9/6257 |
| 2021/0106288 A1* | 4/2021 | Howard | G16H 70/60 |
| 2021/0391061 A1* | 12/2021 | Berlinger | G16H 50/70 |

FOREIGN PATENT DOCUMENTS

| JP | 2007094513 | 4/2007 |
| JP | 2009157527 | 7/2009 |
| WO | 2009050962 | 4/2009 |

OTHER PUBLICATIONS

"Office Action of Japan Counterpart Application" with English translation thereof, issued on Dec. 21, 2021, p. 1 -p. 5.

* cited by examiner

*Primary Examiner* — Oneal R Mistry
(74) *Attorney, Agent, or Firm* — JCIPRNET (57) ABSTRACT

An analysis result acquisition unit acquires an analysis result indicating a certainty factor indicating that an abnormality is included in a medical image by analyzing the medical image. A priority deriving unit derives a higher priority as the certainty factor becomes closer to a median value between a maximum value and a minimum value of the certainty factor.

9 Claims, 4 Drawing Sheets

| | PRIORITY | PATIENT NAME | PATIENT ID | GENDER |
|---|---|---|---|---|
| M | 0.9 | YS | 2000168 | M |
| M | 0.8 | NI | 2000098 | M |
| M | 0.7 | MS | 1000256 | F |
| M | 0.5 | NF | 1000345 | M |
| ⋮ | ⋮ | ⋮ | ⋮ | ⋮ |

FIG. 5

PRIORITY JUDGEMENT DEVICE, METHOD, AND PROGRAM

CROSS REFERENCE TO RELATED APPLICATIONS

The present application claims priority under 35 U.S.C. § 119 to Japanese Patent Application No. 2018-217754 filed on Nov. 20, 2018. The above application is hereby expressly incorporated by reference, in its entirety, into the present application.

BACKGROUND

Technical Field

The present disclosure relates to priority judgement device, method, and program which judge a priority at the time of radiologic interpretation of a medical image and examining, diagnosing, and treating a patient by using the medical image.

Related Art

In recent years, with advances in medical devices such as a computed tomography (CT) device and a magnetic resonance imaging (MRI) device, it is possible to perform image diagnosis by using a medical image with higher quality and high resolution. In particular, in a case where the brain is used as a target part, since it is possible to specify a region in which a vascular disorder such as a cerebral infarction or cerebral hemorrhage occurs by performing image diagnosis using a CT image and an MRI image, it is possible to appropriately perform treatment based on the specified result.

A bleeding region, an infarct region, and a bleeding volume within the brain and an ischemic region in the heart are extracted by analyzing the medical image through computer-aided diagnosis (CAD) using a discriminator that learns through deep learning, and the extracted regions are acquired as these analysis results. As stated above, the analysis results generated by an analysis process are stored in association with examination information such as a patient name, a gender, an age, and a modality that acquires the medical image in a database, and the stored analysis results are used for diagnosis. In this case, a technician of a radiology department that acquires the medical image determines a radiologist corresponding to the medical image, and notifies the determined radiologist of the medical image and the analysis result through the CAD. The radiologist interprets the medical image while referring to the delivered medical image and analysis result, and creates a radiologic interpretation report in a radiologic interpretation terminal of the radiologist.

Here, a score indicating that each pixel of the medical image includes an abnormality such as lesion, bleeding, and infarction is output as a value of, for example, 0 or more and 1 or less by analyzing the medical image through the CAD. The CAD outputs a certainty factor indicating that an abnormality is included in the medical image based on a representative value (for example, an average value and a maximum value) of the scores of the pixels included an abnormal region. For example, there is a very low possibility that the abnormality is to be included in a case where the certainty factor is 0, and there is a very high possibility that the abnormality is to be included in a case where the certainty factor is 1. Thus, the radiologist can interpret the medical image while predicting a degree of abnormality in the medical image by referring to the certainty factor output by the CAD.

A radiologic interpretation list of the medical image to be interpreted is sent to a radiologic interpretation terminal at the time of radiologic interpretation of the medical image. The aforementioned examination information is included in the radiologic interpretation list. As stated above, at the time of displaying the radiologic interpretation list on the radiologic interpretation terminal, a method of displaying the medical image desired to be interpreted on a higher layer of the radiologic interpretation list is suggested (see JP2007-094513A). In the method described in JP2007-094513A, an order of examinations to be interpreted is determined based on status information indicating a priority order of emergency, urgent, and normal radiologic interpretations.

Meanwhile, the use of a learned discriminator is considered in order to determine the priority order at the time of radiologic interpretation. In this case, it is necessary to prepare a large number of medical images and learning data of which a radiologic interpretation priority for the medical image is known in order to cause the discriminator to learn. However, since an operation for collecting such learning data is a difficult task, it is difficult to generate a discriminator that discriminates a radiologic interpretation priority from the medical image. Since the priority for the radiologic interpretation of the medical image largely depends on the discretion of a doctor, it is difficult to determine the radiologic interpretation priority for general purpose.

In the case of an abnormality capable of being easily found by the radiologist in the medical image, a certainty factor output by the CAD becomes higher. Thus, the abnormality capable of being easily found in the medical image can be easily found by the radiologist even though the radiologist does not refer to the certainty factor through the CAD. Meanwhile, in a case where it is difficult to extremely see a region of the abnormality or a very rate lesion is caused, the certainty factor has a value which is neither large nor small. Since there is a possibility that the radiologist is to hesitate about determining whether or not the abnormality is included or is to overlook the abnormality at the time of interpretation, it is necessary to perform more careful interpretation for such a medical image.

SUMMARY OF THE INVENTION

The present disclosure has been made in view of the aforementioned circumstances, and an object of the present disclosure is to appropriately judge a priority at the time of radiologic interpretation of a medical image and examining, diagnosing, and treating a patient by using the medical image.

There is provided a priority judgement device comprising an analysis result acquisition unit that acquires an analysis result indicating a certainty factor indicating that an abnormality is included in a medical image as a priority judgement target, and a priority deriving unit that derives a higher priority as the certainty factor becomes closer to a median value between a maximum value and a minimum value of the certainty factor.

The priority judgement device according to the present disclosure may further comprises an image analysis unit that generates the analysis result by analyzing the medical image.

The priority judgement device according to the present disclosure may further comprise a display controller that displays information regarding the medical image and information of the priority in association with each other for a plurality of the medical images.

In the priority judgement device according to the present disclosure, the priority deriving unit may receive setting of the median value.

A priority judgement method according to the present disclosure comprises acquiring an analysis result indicating a certainty factor indicating that an abnormality is included in a medical image as a priority judgement target, and deriving a higher priority as the certainty factor becomes closer to a median value between a maximum value and a minimum value of the certainty factor.

There is provided a program causing a computer to execute a priority judgement method according to the present disclosure.

There is provided a priority judgement device comprising a memory that stores a command to be executed by a computer; and a processor configured to execute the stored command. The processor acquires an analysis result indicating a certainty factor indicating that an abnormality is included in a medical image as a priority judgement target, and performs a process of deriving a higher priority as the certainty factor becomes closer to a median value between a maximum value and a minimum value of the certainty factor.

According to the present disclosure, it is possible to appropriately judge the priority at the time of radiologic interpretation of a medical image by using an analysis result of the medical image and examining, diagnosing, and treating a patient by using the medical image.

DETAILED DESCRIPTION

Figure 1:
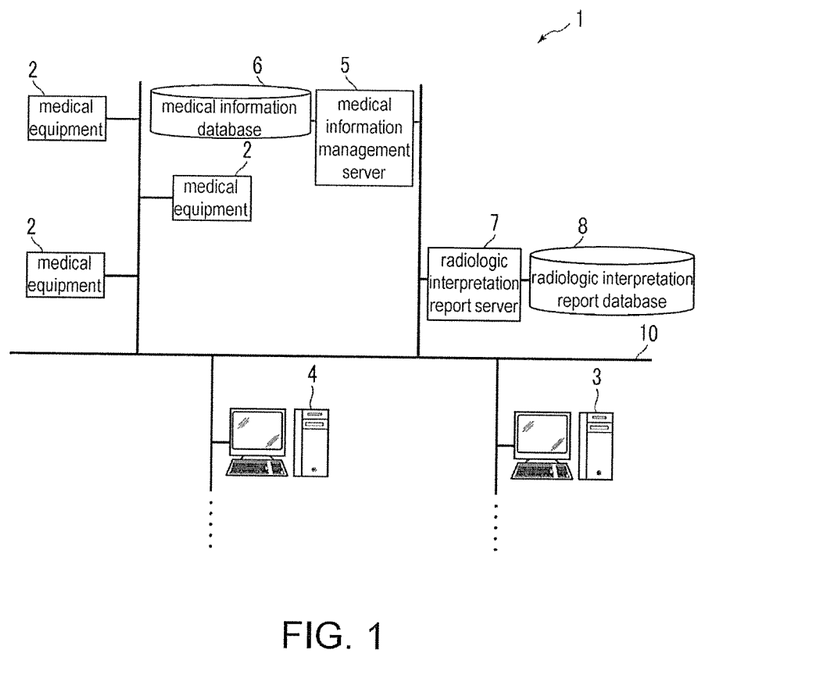
FIG. 1 is a diagram showing a schematic configuration of a medical information system to which a priority judgement device according to an embodiment of the present disclosure.

Hereinafter, an embodiment of the present disclosure will be described with reference to the drawings. FIG. 1 is a diagram showing a schematic configuration of a medical information system to which a priority judgement device according to the embodiment of the present disclosure is applied. A medical information system 1 shown in FIG. 1 is a system that performs imaging of an examination target part of a patient which is a subject, storing of a medical image obtained by imaging, radiologic interpretations and creation of a radiologic interpretation report by a radiologist, viewing of the interpretation report and detailed observation of the medical image of the radiologic interpretation target by the doctor of the hospital department as a requestor based on examination data from a doctor of a hospital department using a known ordering system.

As shown in FIG. 1, the medical information system 1 is configured such that a plurality of modalities 2, a plurality of workstations (WSs) 3 which is radiologic interpretation terminals, hospital department workstations (WSs) 4, a medical information management server 5, a medical information database 6, a radiologic interpretation report server 7, and a radiologic interpretation report database 8 are connected so as to be communicated with each other via a network 10.

Each device is a computer on which an application program for causing the computer to function as components of the medical information system 1 is installed. The application program is distributed while being recorded in a recording medium such as a digital versatile disc (DVD) or a compact disc read only memory (CD-ROM), and is installed on the computer from the recording medium. Alternatively, the application program is stored in a storage device of a server computer connected to a network or a network storage so as to be accessible from the outside, and is downloaded to and installed on the computer if necessary.

The modality 2 is a device that acquires the medical image indicating a diagnostic target part by imaging a part as the diagnostic target of the subject. Specifically, a CT device, an MRI device, a positron emission tomography (PET) device, and a computed radiography (CR) device.

The radiologic interpretation WS 3 is a computer used by the radiologist of the medical image in order to image the medical image and create the radiologic interpretation report, and includes a processing unit, a display unit such as a high-definition display, and an input unit such as a keyboard and a mouse. The radiologic interpretation WS 3 includes the priority judgement device according to the present embodiment. The priority judgement device according to the present embodiment will be described below. In the radiologic interpretation WS 3, various processes such as a viewing request for the medical image to be transmitted to the medical information management server 5, various image processing on the medical image received from the medical information management server 5, supporting for the creation of the radiologic interpretation report, a registration request and a viewing request of the radiologic interpretation report to be transmitted to the radiologic interpretation report server 7, and displaying of the radiologic interpretation report received from the radiologic interpretation report server 7 are performed by executing software programs for the various processes. Among these processes, since processes other than the processes performed by the priority judgement device according to the present embodiment are performed by the known software programs, the detailed description will be omitted.

The hospital department WS 4 is a computer used by the doctor of the hospital department in order to perform the detailed observation of the image, the viewing of the radiologic interpretation report, and the creation of an electronic medical record, and includes a processing unit, a display unit such as a high-definition display, and an input unit such as a keyboard and a mouse. In the hospital department WS 4, various processes such as a viewing request for the medical information to be transmitted to the medical information management server 5, displaying of the medical information received from the medical information management server 5, a viewing request for the radiologic interpretation report to be transmitted to the radiologic interpretation report server 7, and displaying of the radiologic interpretation report received from the radiologic interpretation report server 7 are performed b executing software programs for the various processes.

The medical information management server 5 is realized by installing a software program that provides a function of a database management system (DBMS) on a general-purpose computer. The medical information management server 5 includes a large-capacity storage constituted by the medical information database 6. This storage may be a large-capacity hard disk device connected to the medical information management server 5 via a data bus, or may be a disk device connected to a network attached storage (NAS) and a storage area network (SAN) connected to the network 10. In a case where a registration request for medical information of the medical image from the modality 2 is received, the medical information management server 5 arranges the medical information in a database format, and registers the medical information in the medical information database 6.

In a case where the viewing request for the medical image from the radiologic interpretation WS 3 and the hospital department WS 4 is received via the network 10, the medical information management server 5 searches for the medical image registered in the medical information database 6, and transmits the searched medical image to the radiologic interpretation WS 3 and the hospital department WS 4 which are requesting sources.

Image data of the medical image acquired in the modality 2 is registered in the medical information database 6. Examination information is given, as accessory information, to the medical image. The accessory information includes, for example, an image identification (ID) for identifying an individual medical image, a patient ID for identifying a patient, an examination ID for identifying an examination, an examination date when the medical image is generated, an examination time, the kind of the modality used for the examination for acquiring the medical image, patient information such as a patient name, an age, and a gender, an examination part (imaged part), imaging information (imaging protocol, imaging sequence, imaging method, imaging condition, and using of a contrast agent), and information such as a series number or a collection number at the time of acquiring a plurality of medical images in one examination. At the time of acquiring the plurality of medical images in one examination, the plurality of medical images may be acquired by different modalities 2. For example, both a CT image and an MRI image may be acquired in one examination.

An analysis result for the medical image is registered, as the medical information, in the medical information database 6. The analysis result for the medical image may be acquired in the priority judgement device included in the radiologic interpretation WS 3 to be described below, or may be acquired in an analysis device which is provided separately from the priority judgement device and is connected to the network 10. In a case where the medical image can be analyzed in the hospital department WS 4, the analysis result may be acquired in the hospital department WS 4.

The radiologic interpretation report server 7 is realized by installing a software program that provides a function of the database management system (DBMS) on the computer. In a case where a registration request for the radiologic interpretation report from the radiologic interpretation WS 3 is received, the radiologic interpretation report server 7 arranges the radiologic interpretation report in a database format, and registers the radiologic interpretation report in the radiologic interpretation report database 8.

For example, a radiologic interpretation report that records information such as an image ID for identifying the medical image of the radiologic interpretation target, a radiologist ID for identifying the radiologist who performs the radiologic interpretation, a lesion name, positional information of a lesion, a medical opinion, and a certainty factor of the medical opinion is registered in the radiologic interpretation report database 8.

As stated above, the priority judgement device according to the present embodiment is included in the radiologic interpretation WS 3. Thus, a priority judgement program according to the present embodiment is installed on the radiologic interpretation WS 3. The priority judgement program is distributed while being recorded in a recording medium such as DVD or CD-ROM, and is installed on a computer constituting the radiologic interpretation WS 3 from the recording medium. Alternatively, the application program is stored in a storage device of a server computer connected to a network or a network storage so as to be accessible from the outside, and is downloaded to and installed on the computer.

Figure 2:
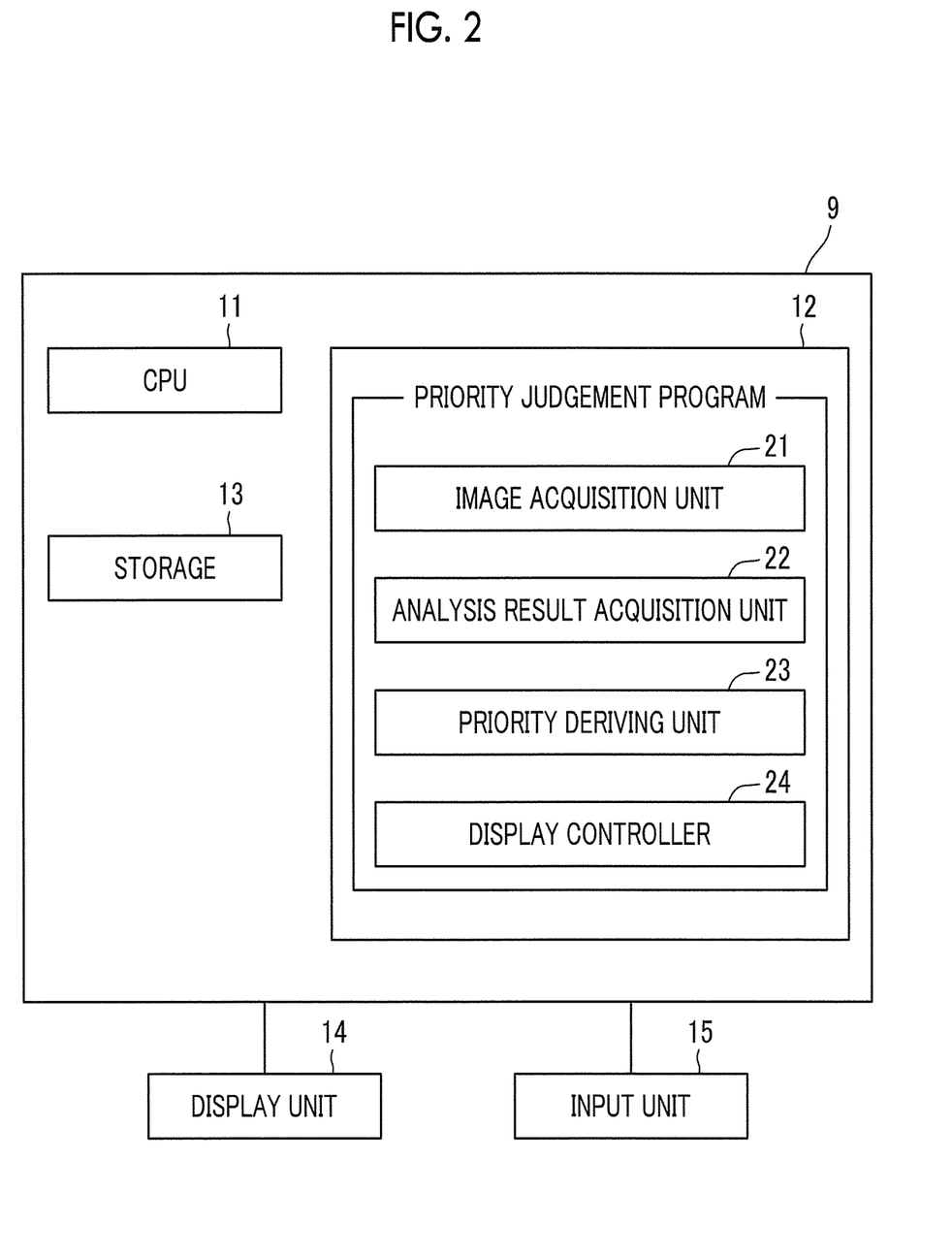
FIG. 2 is a diagram showing a schematic configuration of the priority judgement device according to the embodiment of the present disclosure.

FIG. 2 is a diagram showing a schematic configuration of the priority judgement device according to the present embodiment which is realized by installing the priority judgement program on the computer. As shown in FIG. 2, a priority judgement device 9 includes a central processing unit (CPU) 11, a memory 12, and a storage 13. A display unit 14 such as a liquid crystal display and an input unit 15 such as a keyboard and a mouse are connected to the priority judgement device 9.

The storage 13 is a storage device such as a hard disk or a solid state drive (SSD). Various information including the medical image and information required in the processing which are acquired from the medical information management server 5 via the network 10 are stored in the storage 13.

The priority judgement program is stored in the memory 12. The priority judgement program defines, as processes to be executed by the CPU 11, an image acquiring process of acquiring the medical image of the patient as a priority judgement target from the medical information management server 5, analysis result acquiring process of acquiring an analysis result indicating a certainty factor indicating that an abnormality is included in the medical image by analyzing the medical image, a priority deriving process of deriving a higher priority as the certainty factor becomes closer to a median value between a maximum value and a minimum value of the certainty factor, and a display control process of displaying information regarding the medical image and information of the priority in association with each other on the display unit 14.

The CPU 11 executes these processes according to the program, and thus, the computer functions as an image acquisition unit 21, an analysis result acquisition unit 22, a priority deriving unit 23, and a display controller 24.

In a case where the radiologic interpretation WS 3 functions as a device that performs the processes other than the priority judgement device 9, the program for executing the function thereof is executed. For example, in a case where the radiologic interpretation of the medical image is performed, a radiologic interpretation program is executed.

The image acquisition unit 21 is a communication interface that communicates with the medical information management server 5 via the network 10, and acquires a medical image G0 of a patient as the priority judgement target from the medical information database 6 through the medical information management server 5 according to a command of the priority judgement program. In the present embodiment, the medical image is a CT image of the brain, but may be an MRI image.

The analysis result acquisition unit 22 acquires an analysis result R0 indicating a certainty factor indicating that an abnormality is included in the medical image G0 by analyzing the medical image G0. In the present embodiment, the analysis result acquisition unit 22 acquires an analysis result indicating a certainty factor indicating that each pixel (voxel) of the medical image G0 is infarcted. Thus, the analysis result acquisition unit 22 includes a discriminator that performs machine learning so as to discriminate whether or not each pixel (voxel) of the CT image is infarcted. In the present embodiment, the discriminator is a neural network which performs deep learning so as to discriminate an infarcted region included in the medical image G0 which is the CT image. In a case where the medical image G0 which is the CT image is input, the discriminator learns so as to output a score indicating that each pixel (voxel) within the medical image G0 is infarcted. Here, the score is, for example, a value of 0 or more and 1 or less, and as the value becomes larger, the certainty factor indicating that the pixel is infarcted becomes higher.

For example, the discriminator may be support vector machines (SVM), an AdaBoost, and random forests in addition to the neural network that performs deep learning.

The analysis result acquisition unit 22 acquires the analysis result R0 indicating the certainty factor based on the score of each pixel of the medical image G0. For example, a representative value of the scores of all the pixels of the medical images G0 may be acquired as the certainty factor. An average value, a median value, a maximum value, and a minimum value of the scores may be used as the representative value. A representative value of scores for only regions in which the scores are equal to or greater than a predetermined threshold value may be used as the certainty factor.

The analysis result acquisition unit 22 includes the discriminator, but the acquisition of the certainty factor is not limited to the using of the discriminator.

Figure 3:
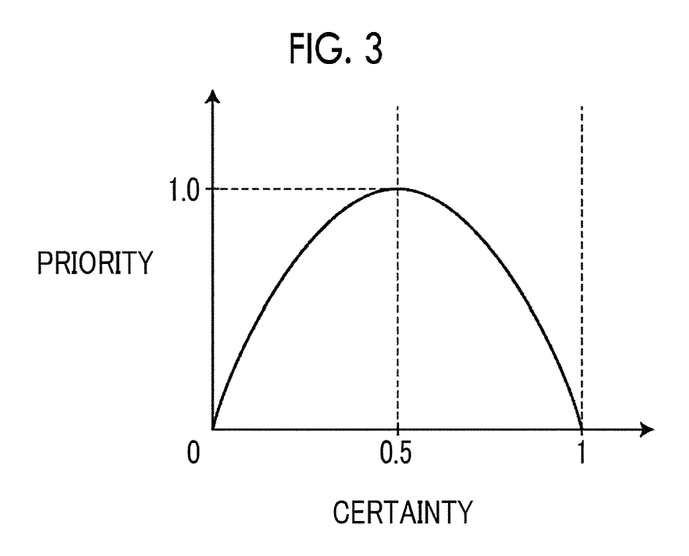
FIG. 3 is a diagram showing a relationship between a certainty factor and a priority.

The priority deriving unit 23 derives a higher priority as the analysis result R0 indicating the certainty factor acquired by the analysis result acquisition unit 22 becomes closer to a median value between a maximum value and a minimum value of a value to be acquired as the certainty factor. In the present embodiment, since the score output by the discriminator is 0 or more and 1 or less, the maximum value to be acquired as the certainty factor is 1, and the minimum value is 0. Thus, in the present embodiment, the median value is set as 0.5. FIG. 3 is a diagram showing a relationship between the certainty factor and the priority. As shown in FIG. 3, the priority with respect to the certainty factor is quadratically changed such that the priority is 0 in a case where the certainty factor is 0 and 1 and the maximum value is 1.0 in a case where the certainty factor is 0.5. The change of the priority with respect to the certainty factor is not limited thereto, and the priority with respect to the certainty factor may be linearly or cubically changed. The median value is not necessarily an exact median value, and may be a value deviated from the median value by about ±10%, or may be the median value.

The priority deriving unit 23 can optionally set the median value according to an input from the input unit 15. For example, the median value may be set as 0.6, and may be set as 0.7.

Figure 4:
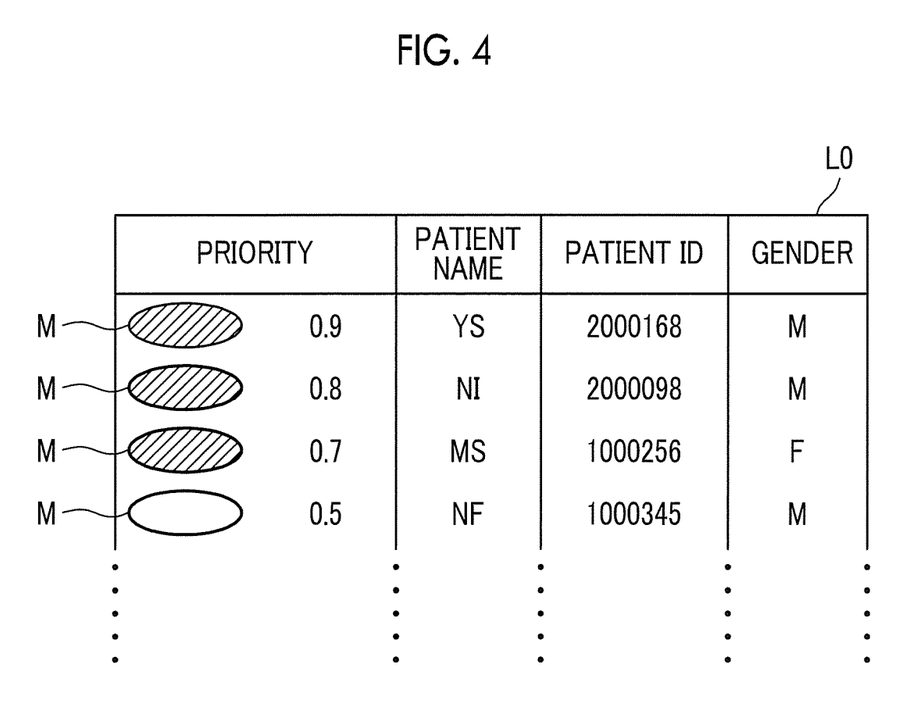
FIG. 4 is a diagram showing a list of information regarding a medical image and information of a priority.

The display controller 24 generates a list in which the information regarding the medical image G0 and the information of the priority are associated with each other for the plurality of medical images, and displays the generated list on the display unit 14. FIG. 4 is a diagram showing the list in which the information regarding the medical image and the information of the priority are associated with each other. A priority, a patient name, a patient ID, and a gender are included in a list L0 as shown in FIG. 4. The information included in the list is not limited thereto, and may include information such as an examination date, an examination technician, and a doctor.

A priority column in the list L0 indicates the priority derived by the priority deriving unit 23. A mark M having a horizontally long oval shape is represented in the priority column. The display controller 24 gives a color to the mark M for the medical image of which the priority is equal to or greater than a predetermined threshold value Th1. In FIG. 4, a state in which the color is given is depicted by a diagonal line. For example, any color such as red and yellow may be used as the color. The patient name of which the priority is equal to or greater than the threshold value Th1 may be turned on and off by changing the color. For example, the threshold value Th1 is set as 0.6 in FIG. 4. Thus, any color is not given to the mark M of the medical image of which the priority is less than the threshold value Th1. Accordingly, the radiologist can recognize which medical image of the plurality of medical images included in the list L0 is to be preferentially interpreted by seeing the list L0 displayed on the display unit 14.

The network 10 is a wired or wireless local area network that connects various devices within a hospital. In a case where the radiologic interpretation WS 3 and the hospital department WS 4 are installed in another hospital or a clinic, the network 10 may connect local area networks of hospitals via the Internet or a dedicated line.

Figure 5:
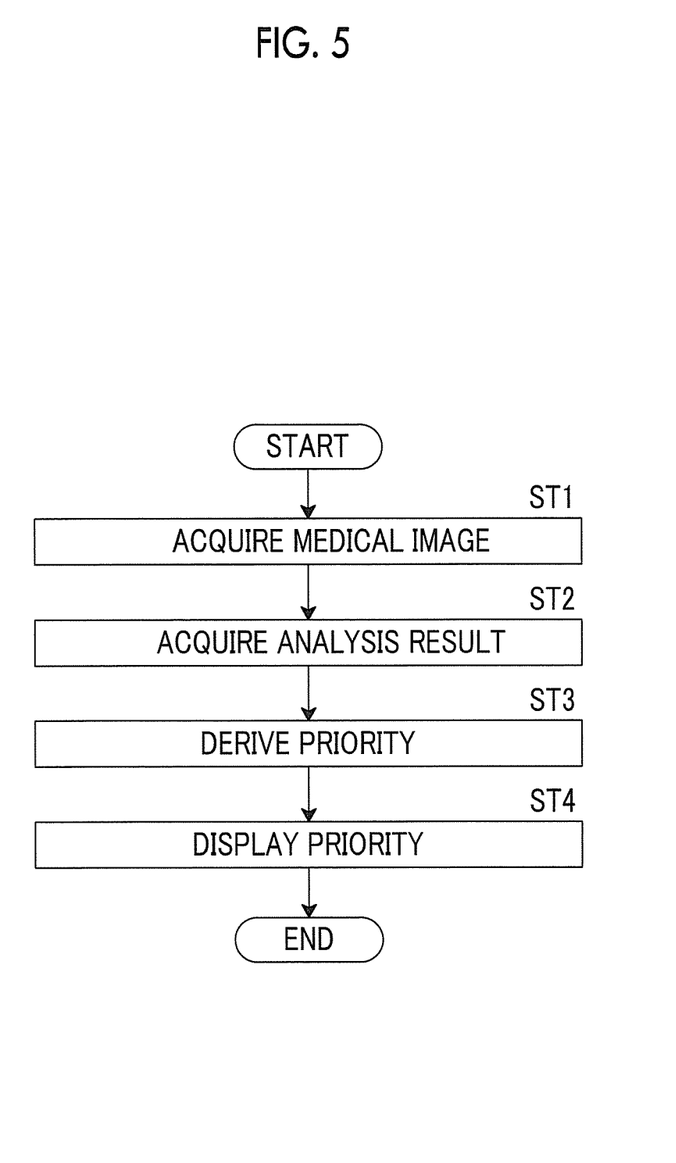
FIG. 5 is a flowchart showing processes performed in the present embodiment.

Next, processes performed in the present embodiment will be described. FIG. 5 is a flowchart showing processes performed by the priority judgement device 9 included in the radiologic interpretation WS 3 in the present embodiment. Initially, the image acquisition unit 21 acquires the medical image G0 of the patient as the priority judgement target (step ST1). Subsequently, the analysis result acquisition unit 22 acquires the analysis result R0 indicating the certainty factor indicating that the abnormality is included in the medical image G0 by analyzing the medical image G0 (step ST2). The priority deriving unit 23 derives a higher priority as the certainty factor becomes closer to the median value between the maximum value and the minimum value of the certainty factor (step ST3). The display controller 24 displays the information regarding the medical image and the information of the priority in association with each other for the plurality of medical images on the display unit 14 (priority display; step ST4), and ends the process.

As stated above, in the present embodiment, the analysis result R0 indicating the certainty factor indicating that the abnormality is included in the medical image G0 of the patient is acquired, and the higher priority as the certainty factor becomes closer to the median value between the maximum value and the minimum value of the certainty factor is derived. Thus, it is possible to increase the priority of the medical image having a possibility that the radiologist is to hesitate about determining whether or not the abnormality is included or is to overlook the abnormality at the time of interpretation. Therefore, according to the present embodiment, it is possible to appropriately judge the priority at the time of the radiologic interpretation of the medical image by using the analysis result R0 of the medical image G0 and examining, diagnosing, and treating the patient by using the medical image.

In particular, since the list in which the information regarding the medical image and the information of the priority are associated with each other for the plurality of medical images is generated and the generated list is displayed on the display unit 14, the radiologist can easily recognize which medical image of the plurality of medical images is to be preferentially interpreted.

In the aforementioned embodiment, the priority derived by the priority deriving unit 23 may be transmitted to the medical information management server 5, and may be registered in association with the medical image in the medical information database 6. Accordingly, the terminal such as the hospital department WS 4 other than the radiologic interpretation WS 3 connected to the network 10 can generate the list L0 shown in FIG. 4 similar to the radiologic interpretation WS 3, and display the generated list by acquiring the priority together with the medical image. In the aforementioned embodiment, the list L0 generated by the display controller 24 may be registered in the medical information database 6. Accordingly, the terminal such as the hospital department WS 4 other than the radiologic interpretation WS 3 connected to the network 10 can display the list L0 shown in FIG. 4 by acquiring the list L0. Accordingly, a medical examiner can easily recognize which patient for the medical image is acquired is to be preferentially diagnosed and treated.

Although it has been described in the aforementioned embodiment that the analysis result acquisition unit 22 of the priority judgement device 9 acquires the analysis result by analyzing the medical image G0, the present disclosure is not limited thereto. The medical image may be analyzed by an analysis device provided separately from the priority judgement device 9, and the analysis result acquired by the analysis device may be acquired by the analysis result acquisition unit 22. The hospital department WS 4 may analyze the medical image. In such a case, the analysis result acquired by the hospital department WS 4 may be acquired by the analysis result acquisition unit 22 of the priority judgement device 9. In a case where the analysis result is registered in the medical information database 6, the analysis result acquisition unit 22 may acquire the analysis result from the medical information database 6.

In the aforementioned embodiment, the priority judgement program according to the present embodiment may be installed on the hospital department WS 4. In this case, the priority is derived in the hospital department WS 4, and the information of the priority and the information of the medical image are displayed in association with each other.

In the aforementioned embodiment, a dedicated terminal that executes the priority judgement program according to the present embodiment may be separately installed as the priority judgement device. In this case, the priority derived in the priority judgement device separately installed is registered in the medical information database 6, and is used for generating and displaying the list L0 shown in FIG. 4 in the radiologic interpretation WS 3 and the hospital department WS 4. In the priority judgement device separately installed, the list L0 may be generated, and may be registered in the medical information database 6.

In the aforementioned embodiment, for example, various processors to be described below can be used as hardware structures of the processing units that perform various processes such as the image acquisition unit 21, the analysis result acquisition unit 22, the priority deriving unit 23, and the display controller 24. As stated above, examples of various processors include a programmable logic device (PLD) such as a field-programmable gate array (FPGA) which is a processor of which a circuit configuration can be changed after being manufactured, a dedicated electric circuit such as an application specific integrated circuit which is a processor having a circuit configuration designed as a dedicated circuit in order to perform a specific process in addition to the CPU which is a general-purpose processor functioning as various processing units by executing software (program).

One processing unit may be constituted by one of these various processors, or may be constituted by a combination (for example, a combination of a plurality of FPGAs or a combination of the CPU and the FPGA) of the same kind or different kinds of two or more processors. Alternatively, the plurality of processing units may be constituted by one processor.

Firstly, as the example in which the plurality of processing units is constituted by one processor, there is a form in which one processor is constituted by a combination of one or more CPUs and software and this processor functions as the plurality of processing units as represented by computers such as a client and a server. Secondly, there is a form in which a processor that implements the entire system function including the plurality of processing units by one integrated circuit (IC) chip as represented by a system on chip (SoC) is used. As stated above, various processing units are constituted as hardware structure by using one or more of various processors.

More specifically, an electric circuitry acquired by combining circuit elements such as semiconductor elements can be used as the hardware structure of these various processors.

What is claimed is:

1. A priority judgement device comprising:
an image acquisition unit that acquires multiple medical images comprising a first medical image and a second medical image,
an analysis result acquisition unit that acquires multiple analysis results comprising a first analysis result of the first medical image indicating a first certainty factor and acquires a second analysis result of the second medical image indicating a second certainty factor,
wherein the first certainty factor being higher than the second certainty factor indicates that a higher likelihood of biological abnormality exists in the first medical image than in the second medical image and the first certainty factor being lower than the second certainty factor indicates that a lower likelihood of biological abnormality exists in the first medical image than in the second medical image; and
a priority deriving unit that derives a priority for each of the multiple medical images based on how close a respective certainty factor is to a median value of certainty factors of the multiple medical images, wherein
the median value is between a maximum possible value and a minimum possible value of the certainty factor,
a higher priority value is given to the first medical image than to the second medical image as a first absolute distance between the first certainty factor and the median value being smaller than a second absolute distance between the second certainty factor and the median value, and
the first medical image is a higher priority judgement target than the second medical image as the first medical image has a higher priority value than the second medical image.

2. The priority judgement device according to claim 1, further comprising:
an image analysis unit that generates the first analysis result and the second analysis result by analyzing the medical image.

3. The priority judgement device according to claim 1, further comprising:
a display controller that displays information regarding the multiple medical images and information priorities in association with each other for the multiple medical images.

4. The priority judgement device according to claim 1, wherein the priority deriving unit receives a setting of the median value.

5. A priority judgement method comprising:
acquiring multiple medical images comprising a first medical image and a second medical image;
acquiring multiple analysis results comprising a first analysis result of the first medical image that indicating a first certainty factor and acquiring a second analysis result of the second medical image that indicating a second certainty factor,
wherein the first certainty factor being higher than the second certainty factor indicates that a higher likelihood of biological abnormality exists in the first medical image than in the second medical image and the first certainty factor being lower than the second certainty factor indicates that a lower likelihood of biological abnormality exists in the first medical image than in the second medical image; and
deriving a priority for each of the multiple medical images based on how close a respective certainty factor is to a median value of certainty factors of the multiple medical images, wherein
the median value is between a maximum possible value and a minimum possible value of the certainty factor,
a higher priority is given to the first medical image than to the second medical image as a first absolute distance between the first certainty factor and the median value being smaller than a second absolute distance between the second certainty factor and the median value, and
the first medical image is a higher priority judgement target than the second medical image as the first medical image has a higher priority value than the second medical image.

6. A non-transitory computer-readable storage medium that stores a priority judgement program causing a computer to execute:
acquiring multiple medical images comprising a first medical image and a second medical image;
acquiring multiple analysis results comprising a first analysis result of the first medical image that indicating a first certainty factor indicating and acquiring a second analysis result of the second medical image indicating a second certainty factor,
wherein the first certainty factor being higher than the second certainty factor indicates that a higher likelihood of biological abnormality exists in the first medical image than in the second medical image and the first certainty factor being lower than the second certainty factor indicates that a lower likelihood of biological abnormality exists in the first medical image than in the second medical image; and
deriving a priority for each of the multiple medical images based on how close a respective certainty factor is to a median value of certainty factors of the multiple medical images, wherein
the median value is between a maximum possible value and a minimum possible value of the certainty factor,
a higher priority is given to the first medical image than to the second medical image as a first absolute distance between the first certainty factor and being smaller than a second absolute distance between the second certainty factor and the median value, and
the first medical image is a higher priority judgement target than the second medical image as the first medical image has a higher priority value than the second medical image.

7. The priority judgement device of claim 1, wherein the median value is the middle value of the maximum possible value and the minimum possible value.

8. The priority judgement device of claim 1, wherein the median value is an arbitrarily selected value which is between the maximum possible value and the minimum possible value.

9. The priority judgement device of claim 1 further comprises a display controller that displays a plurality of priority values of the multiple medical images, and priority values of medical images of the multiple medical images exceeding a threshold value are displayed differently from priority values of other medical images of the multiple medical images not exceeding the threshold value.

* * * * *